US00PP31667P2

(12) United States Plant Patent
Danziger

(10) Patent No.: US PP31,667 P2
(45) Date of Patent: Apr. 14, 2020

(54) ***ERYSIMUM* PLANT NAMED 'DERSUSGBP'**

(50) Latin Name: *Erysimum linifolium*
Varietal Denomination: DERSUSGBP

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 16/501,677

(22) Filed: May 21, 2019

(51) Int. Cl.
*A01H 5/02* (2018.01)
*A01H 6/20* (2018.01)

(52) U.S. Cl.
USPC ..... Plt./263.1

(58) Field of Classification Search
USPC ..... Plt./263.1
CPC ..... A01H 5/02; A01H 6/20
See application file for complete search history.

*Primary Examiner* — Annette H Para
(74) *Attorney, Agent, or Firm* — Cassandra Bright

(57) ABSTRACT

A new and distinct *Erysimum* cultivar named 'DERSUSGBP' is disclosed, characterized by abundant flowers occurring on an upright, vigorous plant. Plants do not require vernalization to flower. Flowers are pleasantly scented and begin orange in color, changing to lavender. The new variety is an *Erysimum*, normally produced as an outdoor garden or container plant.

2 Drawing Sheets

Figure 1:
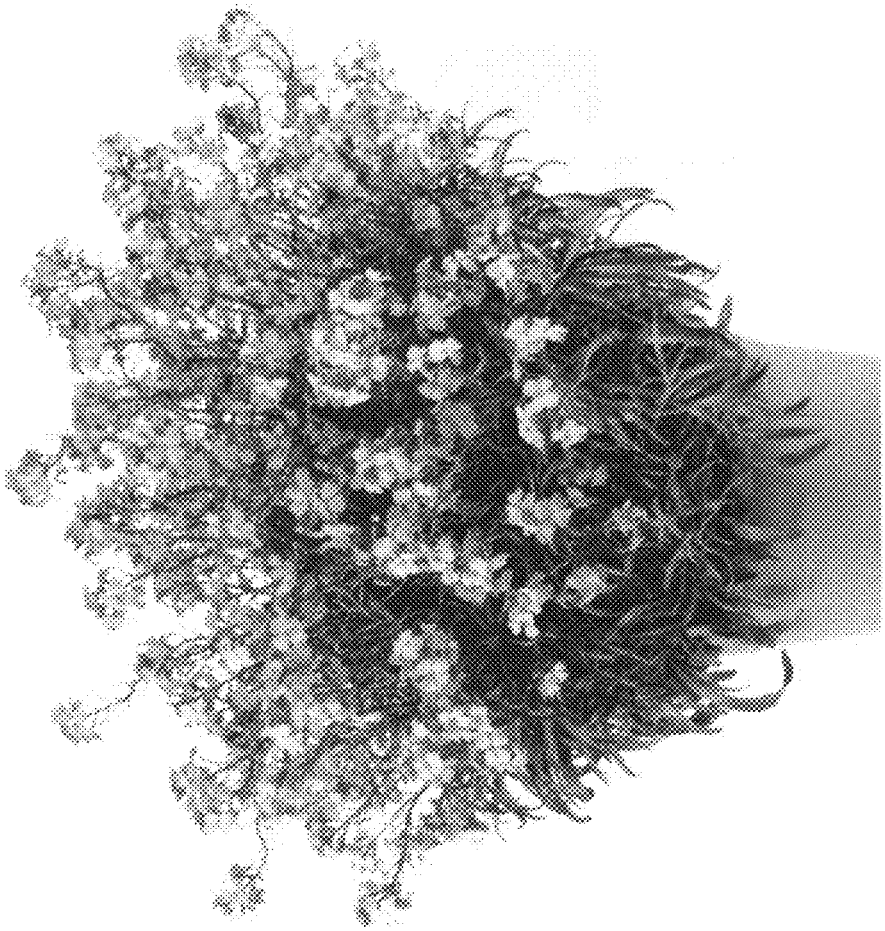

Latin name of the genus and species: *Erysimum linifolium.*

Variety denomination: 'DERSUSGBP'.

BACKGROUND OF THE INVENTION

The new *Erysimum* cultivar is a product of a planned breeding program conducted by the inventor, Gavriel Danziger in Moshav Mishmar Hashiva, Israel. The objective of the breeding program was to produce new *Erysimum* varieties. The open-pollination resulting in this new variety was made during January of 2013.

The seed parent is the, unpatented, propriety variety referred to as *Erysimum* 'ER-12-2'. The pollen parent is unknown, as it was an open-pollination breeding program. The new variety was discovered in October 2014 by the inventor in a group of seedlings resulting from the crossing, in a greenhouse in Moshav Mishmar Hashiva, Israel. Date of first sale was Aug. 3, 2018, occurring in the United States. This sale was made directly by the inventor or one who obtained the claimed invention directly or indirectly from the inventor. This sale and all public disclosures made between Aug. 3, 2018 and the filing of this application fall within the exception allowed under 102(b)(1).

Asexual reproduction of the new cultivar 'DERSUSGBP' first by vegetative cuttings was first performed during November 2014, at a greenhouse in Moshav Mishmar Hashiva, Israel. Subsequent propagation by vegetative cuttings has shown that the unique features of this cultivar are stable and reproduced true to type in multiple successive generations.

SUMMARY OF THE INVENTION

The cultivar 'DERSUSGBP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DERSUSGBP' These characteristics in combination distinguish 'DERSUSGBP' as a new and distinct *Erysimum* cultivar:

1. Flowers without vernalization.
2. Nice scent.
3. Abundant flowering.
4. Upright vigorous plant.

PARENT COMPARISON

Plants of the new cultivar 'DERSUSGBP' are similar to plants of the seed parent in most horticultural characteristics, however, plants of the new cultivar 'DERSUSGBP' differ in the following;

1. 'DERSUSGBP' has larger flowers than 'ER-12-2'.
2. 'DERSUSGBP' has orange flowers when opening and which change to purple flowers, while 'ER-12-2' has light purple flowers.
3. 'DERSUSGBP' has a more upright and tall habit, while 'ER-12-2' is more mounded and compact.
4. 'DERSUSGBP' has nicer fragrance than 'ER-12-2'.

COMMERCIAL COMPARISON

Plants of the new cultivar 'DERSUSGBP' can be compared to the unpatented commercial variety *Erysimum* 'Super Bowl Mauve'. These varieties are similar in most horticultural characteristics; however, 'DERSUSGBP' differs in the following:

1. 'DERSUSGBP' flowers very early and with no vernalization compared with 'Super Bowl Mauve' which requires vernalization.
2. 'DERSUSGBP' has a longer inflorescence than 'Super Bowl Mauve'.
3. 'DERSUSGBP' has darker purple flowers when fully opened than 'Super Bowl Mauve'.

Plants of the new cultivar 'DERSUSGBP' can also be compared to the unpatented commercial variety *Erysimum*

'Poem Lavender'. These varieties are similar in most horticultural characteristics; however, 'DERSUSGBP' differs in the following:

1. 'DERSUSGBP' has larger flowers than 'Poem Lavender'.
2. 'DERSUSGBP' flowers very early and with no vernalization compared with 'Poem Lavender' which requires vernalization.

BRIEF DESCRIPTION OF THE PHOTOGRAPHS

The accompanying photograph in FIG. 1 illustrates in full color a typical plant of 'DERSUSGBP' grown in in a greenhouse, in Moshav Mishmar Hashiva, Israel.

Figure 2:
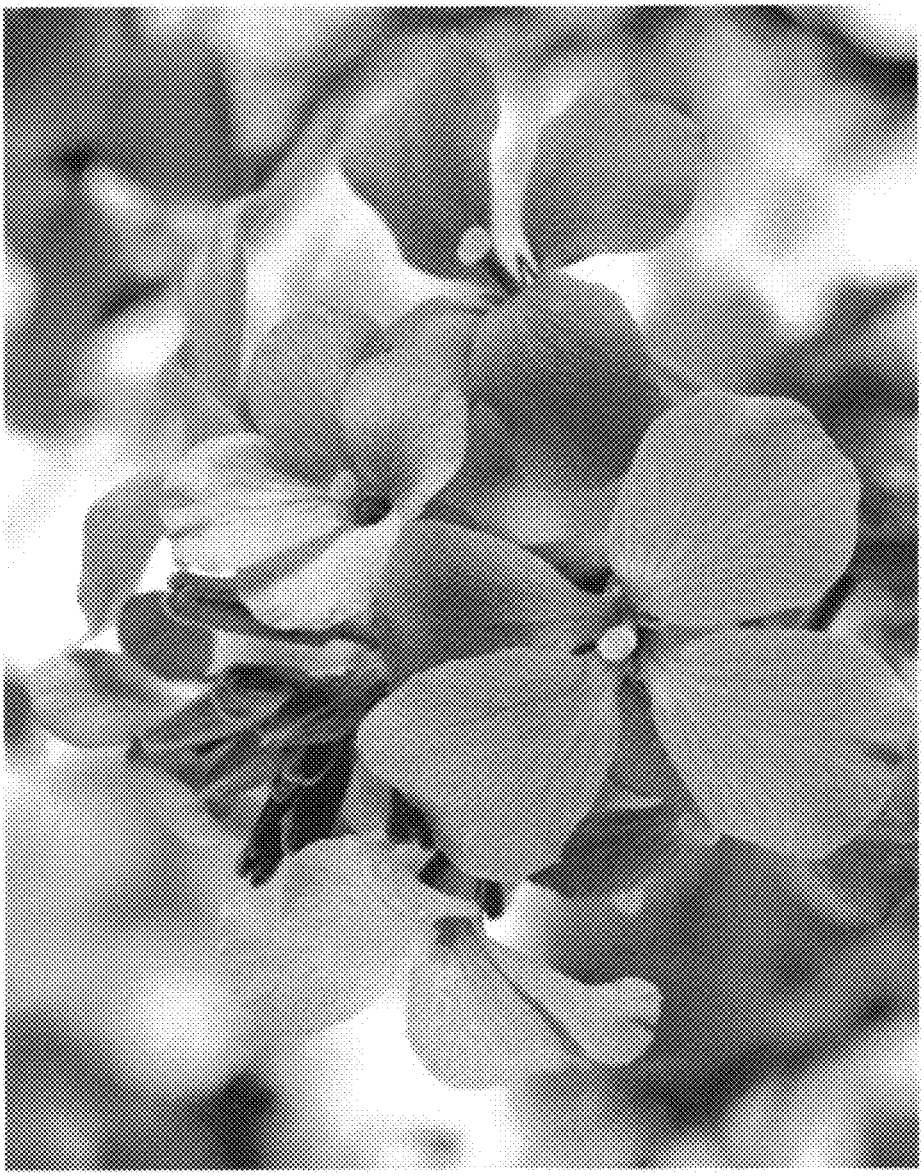

FIG. 2 illustrates in full color a typical inflorescence of 'DERSUSGBP'. Age of the plant photographed is approximately 2 to 3 months old in a 25 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DERSUSGBP' plants grown in a nursery in Moshav Mishmar Hashiva, Israel, under natural lighting. Measurements were taken during April 2019. The plants were approximately 2 to 3 months old in a 25 cm pot. The growing temperature ranged from 18° C. to 28° C. during the days, 13° C. to 18° C. during the nights. Measurements and numerical values represent averages of typical plant types.

Botanical classification: *Erysimum linifolium* 'DERSUSGBP'.

PROPAGATION

Time to initiate roots:

*Summer.*—14 to 21 days at optimal temperature of approximately 25° C.

*Winter.*—21 to 26 days at approximately 22° C.

Root description: White and fibrous.

PLANT

Growth habit: Upright.
Pot size of plant described: 25 cm.
Height: 35-40 cm.
Plant spread: 40-50 cm.
Growth rate: Medium.
Branching characteristics: Well branched pseudomonopodial.
Length of primary lateral branches: 35-40 cm.
Quantity of primary lateral branched: 30.
Characteristics of primary lateral branches:

*Form.*—Ridged.
*Diameter.*—2.5 cm.
*Color.*—RHS Green 137A.
*Texture.*—Slightly palmate.
*Strength.*—Strong, not easily breakable.

Internode length: 2.5 cm.

FOLIAGE

Leaf:

*Arrangement.*—Alternate.
*Quantity.*—Approximately 20 per branch.
*Average length.*—7.5 cm.
*Average width.*—0.6 cm.
*Shape of blade.*—Linear.
*Apex.*—Narrowly.
*Base.*—Attenuate.
*Margin.*—Slight serrate.
*Texture of top surface.*—Slightly pannate.
*Texture of bottom surface.*—Slightly pannate.
*Aspect.*—30-40°.
*Color.*—Young foliage upper side: RHS Green 137A. Young foliage under side: RHS Green 137B. Mature foliage upper side: RHS Green 137A. Mature foliage under side: RHS Green 137B.
*Venation.*—Type: Pinnate. Venation color upper side: RHS Green 137C. Venation color under side: RHS Green 137D.
*Petiole.*—None.

FLOWER

Natural flowering season: Early spring.
Inflorescence type: Spike.
Flower type: Single.
Rate of flower opening: 2 to 5 days from bud to fully opened flower.
Flower longevity on plant: 6-7 days.
Persistent or self-cleaning: Self-cleaning.
Corolla:
Flower size:

*Diameter.*—2.5-3 cm.
*Depth.*—1.5 cm.

Petals:

*Quantity.*—4.
*Arrangement.*—Cross-shaped.
*Lobe length.*—1.5 cm.
*Lobe width.*—1 cm.
*Lobe shape.*—Orbicular.
*Apex.*—Rounded.
*Margin.*—Entire.
*Texture, upper and lower surfaces.*—Straight.
*Color.*—When opening, upper surface: RHS Greyed-Orange 166D. When opening, lower surface: RHS Greyed-Orange 166D. Fully opened, upper surface: RHS Violet N87B. Fully opened, lower surface: RHS Violet N87C. Fading: Slightly fading, RHS Violet N87C.

Tube:

*Length.*—1 cm.
*Width.*—0.5 cm.
*Color.*—When opening, inner surface: RHS Green-Yellow 1D. When opening, outer surface: RHS Green-Yellow 1C. Fully opened, inner surface: RHS Violet 84D. Fully opened, upper surface: RHS Violet 84D.

Fragrance: Nice honey scent.
Bud:

*Shape.*—Ellipsoid.
*Length.*—0.6 cm.
*Diameter.*—0.4 cm.
*Color.*—RHS Greyed-Orange 172A.

Calyx:
*Shape.*—4 lobed fused only at the bottom.
Sepals:
*Quantity.*—4.
*Length.*—1 cm.
*Width.*—0.3 cm.
*Shape* (*overall*).—Oblong.
*Apex*.—Acute.
*Base*.—Cordate.
*Margin*.—Entire.
*Color*.—RHS Yellow-Green 145A.
Peduncles: None.
Pedicels:
*Length.*—0.6 cm.
*Diameter.*—0.1 cm.
*Angle*.—About 40°.
*Strength*.—Strong.
*Texture*.—Velvet.
*Color*.—RHS Yellow-Green 146A.

REPRODUCTIVE ORGANS

Stamens:
*Number.*—6.
Anthers:
*Shape*.—Oblong.
*Length*.—Approximately 0.2 cm.
*Color*.—RHS Yellow-Green 151B.
*Pollen*.—Color: RHS Yellow 4D. Quantity: Scant.
Pistil:
*Number.*—1.
*Length.*—1.6 cm.
*Style*.—Length: 1.1 cm. Color: RHS Yellow-Green 147D.
*Stigma*.—Shape: Oval. Color: RHS Yellow-Green 154A. Ovary Color: RHS Green 137A.

OTHER CHARACTERISTICS

Seeds and fruits: None observed.
Disease/pest resistance: Neither resistance no susceptibility to normal diseases and pests observed.
Temperature tolerance: Tolerates temperatures within USDA Zones 6 through 11.

What is claimed is:

1. A new and distinct cultivar of *Erysimum* plant named 'DERSUSGBP' as herein illustrated and described.

* * * * *